US 8,538,526 B2

(12) United States Patent
Stahmann et al.

(10) Patent No.: US 8,538,526 B2
(45) Date of Patent: Sep. 17, 2013

(54) AUTOMATIC PROGRAMMING OF RATE-ADAPTIVE THERAPY VIA ACTIVITY MONITORING

(75) Inventors: Jeffrey E. Stahmann, Ramsey, MN (US); Michael A. Querimit, Fridley, MN (US); Donald L. Hopper, Maple Grove, MN (US); Brian Ralph Larson, Shoreview, MN (US); Paul F. Emerson, St. Louis Park, MN (US); Daniel O'Brien, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 278 days.

(21) Appl. No.: 12/970,613

(22) Filed: Dec. 16, 2010

(65) Prior Publication Data

US 2011/0152963 A1 Jun. 23, 2011

Related U.S. Application Data

(60) Provisional application No. 61/287,306, filed on Dec. 17, 2009.

(51) Int. Cl.
*A61N 1/365* (2006.01)
(52) U.S. Cl.
USPC .............................................. 607/20; 607/19
(58) Field of Classification Search
USPC ........................................................ 607/19, 20
IPC ........................................................ A61N 1/365
See application file for complete search history.

(56) References Cited

U.S. PATENT DOCUMENTS

| | | | |
|---|---|---|---|
| 6,490,485 B1 | 12/2002 | Sun et al. | |
| 6,823,214 B1 | 11/2004 | Sun et al. | |
| 6,839,593 B1 | 1/2005 | Sun et al. | |
| 2002/0151936 A1* | 10/2002 | Kloss et al. | 607/14 |
| 2003/0204211 A1 | 10/2003 | Condie et al. | |
| 2005/0042589 A1* | 2/2005 | Hatlestad et al. | 434/262 |
| 2006/0265019 A1* | 11/2006 | Sun et al. | 607/19 |
| 2008/0004664 A1 | 1/2008 | Hopper et al. | |

FOREIGN PATENT DOCUMENTS

WO  WO-2011/084635 A1  7/2011

OTHER PUBLICATIONS

"International Application Serial No. PCT/US2010/060839, International Search Report mailed Apr. 8, 2011", 7 pgs.
"International Application Serial No. PCT/US2010/060839, Written Opinion mailed Apr. 8, 2011", 8 pgs.
Newman, A. B., et al., "Walking Performance and Cardiovascular Response: Associations with Age and Morbidity—The Health Aging and Body Composition Study", *Journal of Gerontology*, 58A(8), (2003), 715-720.
Quell, K. J., et al., "Is Brisk Walking an Adequate Aerobic Training Stimulus for Cardiac Patients?", *Chest*, 122, (2002), 1852-1856.

* cited by examiner

*Primary Examiner* — Eric D. Bertram
(74) *Attorney, Agent, or Firm* — Schwegman Lundberg & Woessner, P.A.

(57) ABSTRACT

A rate-adaptive pacemaker and a method for its operation in which the response factor for a minute ventilation sensor or other type of exertion level sensor is automatically set during a parameter adjustment mode that utilizes an activity level measurement to determine when the patient is at a target activity level with which is associated an appropriate target pacing rate. In a preferred embodiment, the target activity level corresponds to casual walking (e.g., 2 mph at a 4% grade) with a target pacing rate selected as appropriate for that level of activity in the individual patient.

14 Claims, 4 Drawing Sheets

AUTOMATIC PROGRAMMING OF RATE-ADAPTIVE THERAPY VIA ACTIVITY MONITORING

CLAIM OF PRIORITY

This application claims the benefit of priority under 35 U.S.C. §119(e) of U.S. Provisional Patent Application Ser. No. 61/287,306, filed on Dec. 17, 2009, which is herein incorporated by reference in its entirety.

FIELD OF THE INVENTION

This invention pertains to systems and methods for cardiac rhythm management. In particular, the invention relates to a system and method for automatically adjusting the operating parameters of a rate-adaptive cardiac pacemaker.

BACKGROUND

A conventional cardiac pacemaker is an implantable battery-powered electronic device that responds to sensed cardiac events and elapsed time intervals by changing its functional states so as to properly interpret sensed data and deliver pacing pulses to the heart at appropriate times. The pacing pulses are delivered through a lead made up of an electrode(s) on a catheter or wire that connects the pacemaker to the heart. Additional sensing of physiological data allows some pacemakers to change the rate at which they pace the heart in accordance with some parameter correlated to metabolic demand. Such pacemakers, which are the primary subject of the present invention, are called rate-adaptive pacemakers.

The most common condition for which pacemakers are used is the treatment of bradycardia. Atrio-ventricular conduction defects (i.e., AV block) that are fixed or intermittent and sick sinus syndrome represent the most common indications for permanent ventricular pacing. Pacemakers may also be employed to deliver cardiac resynchronization therapy (CRT) to patients having ventricular conduction deficits in which paces are delivered one or more ventricular sites in order to cause a more coordinated contraction. In chronotropically competent patients in need of ventricular pacing, atrial tracking modes such as DDD or VDD are desirable because they allow the pacing to track the physiologically normal atrial rhythm, which causes cardiac output to be responsive to the metabolic needs of the body. Atrial tracking modes are contraindicated, however, in patients prone to atrial fibrillation or flutter or in whom a reliable atrial sense cannot be obtained. In pacemaker patients who are chronotropically incompetent (e.g., sinus node dysfunction) or in whom atrial-triggered modes such as DDD and VDD are contraindicated, the heart rate is determined solely by the pacemaker in the absence of intrinsic cardiac activity. That heart rate is determined by the programmed escape intervals of the pacemaker and is referred to as the lower rate limit or LRL.

Pacing the heart at a fixed rate as determined by the LRL setting of the pacemaker, however, does not allow the heart rate to increase with increased metabolic demand. Cardiac output is determined by two factors, the stroke volume and heart rate, with the latter being the primary determinant. Although stroke volume can be increased during exercise, the resulting increase in cardiac output is usually not sufficient to meet the body's metabolic needs unless the heart rate is also increased. If the heart is paced at a constant rate, as for example by a VVI pacemaker, severe limitations are imposed upon the patient with respect to lifestyle and activities. It is to overcome these limitations and improve the quality of life of such patients that rate-adaptive pacemakers have been developed. Rate-adaptive pacemakers operate so as to vary the lowest rate at which the heart is allowed to beat in accordance with one or more physiological parameters related to metabolic demand.

One way to control the rate of a pacemaker is to measure the metabolic rate of the body and vary the pacing rate in accordance with the measurement. Metabolic rate can effectively be directly measured by, for example, sensing blood pH or blood oxygen saturation. Practical problems with implementing pacemakers controlled by such direct measurements, however, have led to the development of pacemakers that are rate-controlled in accordance with physiological variables that are indirectly reflective of the body's metabolic rate such as body temperature, ventilation rate, or minute ventilation. Minute ventilation varies almost linearly with aerobic oxygen consumption during exercise up to the anaerobic threshold and is the physiological variable that is most commonly used in rate-adaptive pacemakers to reflect the exertion level of the patient.

An even more indirect indication of metabolic rate is provided by the measurement of body activity or motion using an accelerometer. Body activity is correlated with metabolic demand because such activity requires energy expenditure and hence oxygen consumption.

In such rate-adaptive pacemakers that vary the pacing rate in accordance with a measured exertion level, the control system is generally implemented as an algorithm that maps a particular exertion level to one particular target heart rate, referred to as the sensor-indicated rate (SIR). The mapping is accomplished by a rate-response curve which is typically a linear function (i.e., a straight line), but could also be some non-linear function as well such as a dual-slope curve or exponential curve. The responsiveness of the control system, defined as how the target heart rate changes with a given change in exertion level, depends upon the slope of the rate-response curve (or slopes in the case of a dual-slope curve), referred to as the response factor. If the response factor is incorrectly defined, the pacemaker's responsiveness will not be set to an appropriate level. An under-responsive pacemaker will unnecessarily limit exercise duration and intensity in the patient because the heart rate will not increase enough to match metabolic demand, while an over-responsive pacemaker can lead to palpitations and patient discomfort.

The usual methods for setting the response factor of rate-adaptive pacemaker involve exercise testing or continuous monitoring to determine the patient's maximum exertion level to which is associated an individually selected maximum pacing rate. Exercise testing may not always be practical, however, and a patient's maximum exercise capacity can change over time due to, e.g., physical conditioning or illness which increases the need for follow-up visits. Algorithms have therefore been developed that attempt to adjust the responsiveness of rate-adaptive pacemakers automatically in accordance with exertion level measurements made as the patient goes about ordinary activity. Determining a patient's maximum exercise capacity from periodic exertion level measurements, however, is problematical since it is not known how close to the true maximum a periodic maximum exertion level is.

DETAILED DESCRIPTION

Described herein is a rate-adaptive pacemaker and a method for its operation in which the response factor for a minute ventilation sensor or other type of exertion level sensor is automatically set during a parameter adjustment mode that utilizes an activity level measurement to determine when the patient is at a target activity level with which is associated an appropriate target pacing rate. The pacemaker is programmed with a specified LRL which is mapped to by the rate-adaptive algorithm when the exertion level measurement corresponds to rest. In order to determine another endpoint of the rate response curve and calculate the response factor, the pacemaker enters the parameter adjustment mode during which the patient's activity level is monitored using an accelerometer or other motion sensor. When the measured activity level falls within a specified target activity level range for a predetermined length of time, the pacemaker measures the corresponding target exertion level (e.g., the minute ventilation). The response factor is then calculated using the LRL and resting exertion level as one endpoint of the rate response curve and the target exertion level and a target pacing rate as the other endpoint, where the target pacing rate appropriate for the target activity level is a programmable parameter. The same response factor may then be used for exertion levels higher than the target exertion level up to the programmed maximum pacing rate or to the curve breakpoint in the case of a dual-slope or other type of rate response curve. In the case of dual-slope rate response curve, the slope of the curve is reduced at the curve breakpoint, usually selected to occur at an exertion level equal to the patient's anaerobic threshold. The calculated response factor may be multiplied by a specified percentage (e.g., 75%) or otherwise decreased to provide a reduced response factor for points on the rate response after the curve breakpoint.

In a preferred embodiment, the target activity level corresponds to casual walking (e.g., 2 mph at a 4% grade) with a target pacing rate selected as appropriate for that level of activity in the individual patient. Casual walking is an activity that can easily and reliably be attained by most patients. By using a submaximal activity level to calibrate the rate-adaptive pacing algorithm, the necessity of strenuous exercise testing and the problems involved with determining a maximum exercise capacity are avoided.

Hardware Description

Figure 1:
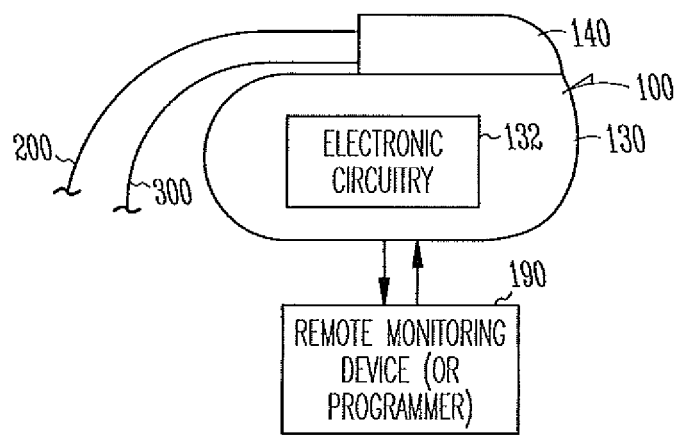
FIG. 1 shows the components of an exemplary device.

Implantable pacing devices are typically placed subcutaneously or submuscularly in a patient's chest with leads threaded intravenously into the heart to connect the device to electrodes disposed within a heart chamber that are used for sensing and/or pacing of the chamber. A programmable electronic controller causes the pacing pulses to be output in response to lapsed time intervals and/or sensed electrical activity (i.e., intrinsic heart beats not as a result of a pacing pulse). FIG. 1 shows the components of an implantable pacing device that includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190.

Figure 2:
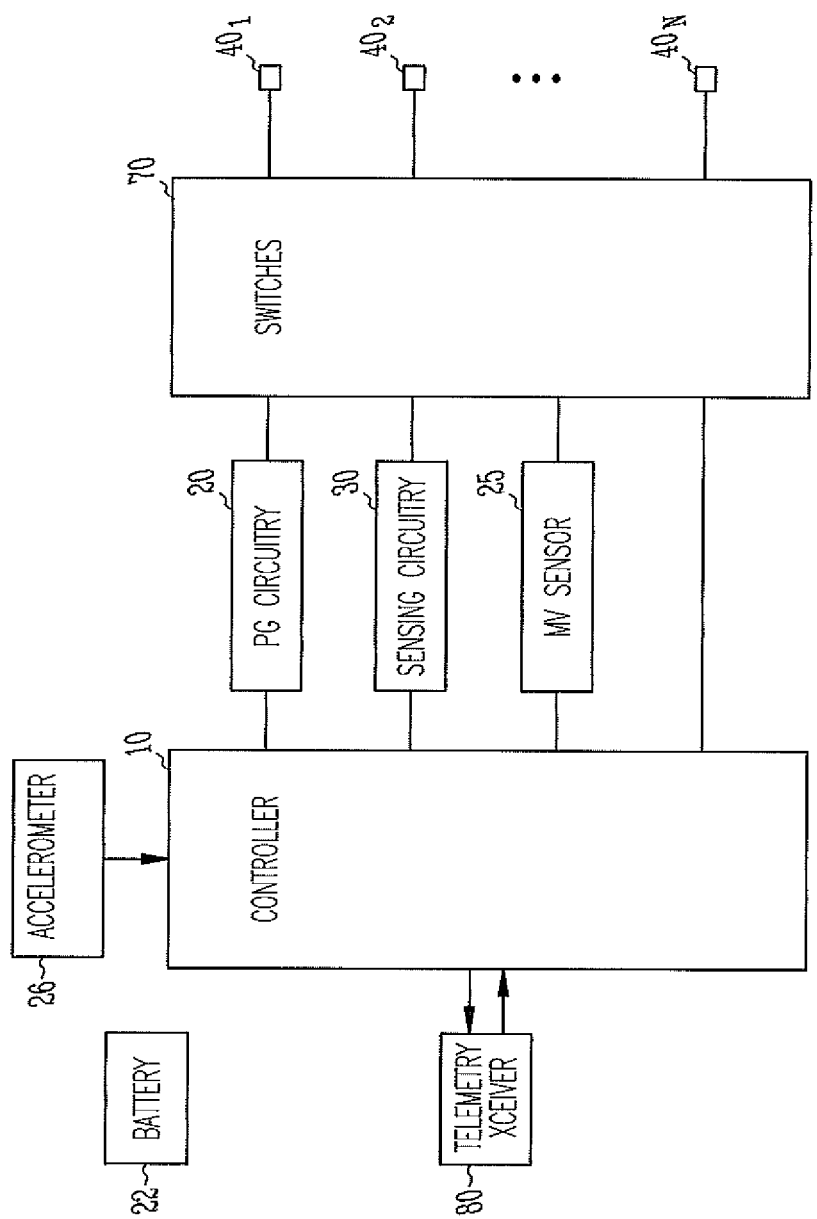
FIG. 2 is a block diagram of the electronic circuitry of an exemplary device.

A block diagram of the circuitry 132 is illustrated in FIG. 2. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. As the term is used herein, the programming of the controller refers to either code executed by a microprocessor or to specific configurations of hardware components for performing particular functions. A telemetry transceiver 80 is interfaced to the controller which enables the controller to communicate with an external programmer and/or a remote monitoring unit. Sensing circuitry 30 and pacing or pulse generation circuitry 20 are interfaced to the controller by which the controller interprets sensing signals and controls the delivery of pacing pulses in accordance with a pacing mode. The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge pulse generators, registers for controlling the pulse generators, and registers for adjusting pacing parameters such as pulse energy (e.g., pulse amplitude and width). The pulse generation circuitry may also include a shocking pulse generator for delivering a defibrillation/cardioversion shock via a shock electrode upon detection of a tachyarrhythmia.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The switch matrix 70 allows selected ones of the available implanted electrodes to be incorporated into sensing and/or pacing channels in either unipolar or bipolar configurations that may be either atrial or ventricular channels depending upon the location of the electrode.

The controller is capable of operating the device in a number of programmed modes where a programmed mode defines how pacing pulses are output in response to sensed events and expiration of time intervals. Pacing may be delivered in conjunction with a bradycardia pacing mode, which refers to a pacing algorithm that enforces a certain minimum heart rate by delivering pacing pulses to the atria or ventricles whether for treating bradycardia or to deliver cardiac resynchronization therapy. Inhibited demand bradycardia pacing modes utilize escape intervals to control pacing in accordance with sensed intrinsic activity. In an inhibited demand pacing mode, an atrium or ventricle is paced during a cardiac cycle only after expiration of a defined escape interval during which no intrinsic beat by the chamber is detected.

The device is also equipped with a minute ventilation sensor 25 for measuring the patient's minute ventilation and an activity level sensor 26. The activity level sensor may be any type of motion detector capable of detecting the number of steps taken during a given time period during walking. Examples of motion detectors include accelerometers and velocity-type sensors such as Hall effect sensors, acoustic sensors, or other types of transducers that respond to changes in the patient's physical activity. In one embodiment, the activity level sensor is an accelerometer inside the pacemaker case that responds to vibrations or accelerations and, after appropriate filtering, produces electrical signals proportional to the patient's level of physical activity. For example, in order to optimally detect casual walking, the accelerometer data may be moving averaged over a 30 second period after filtering to remove high frequency vibrations. The minute ventilation sensor includes a pair of current source electrodes and a pair of voltage sense electrodes for measuring transthoracic impedance. In rate-adaptive pacing, the pacemaker uses the sensed minute ventilation and/or the accelerometer signal to adjust the rate at which the pacemaker paces the heart in the absence of a faster intrinsic rhythm.

Rate-Adaptive Pacing

In rate-adaptive pacemakers that vary the pacing rate in accordance with a measured exertion level, the control system is generally implemented as an open-loop controller that maps a particular exertion level to one particular target heart rate, termed the sensor-indicated rate or SIR. The SIR is the rate at which the heart (either the atria or ventricles) is paced in the absence of faster intrinsic activity. The mapping is accomplished by a rate-response curve which is typically a linear function (i.e., a straight line), but could also be some non-linear function as well such as a dual-slope curve or exponential curve. The rate-response curve is then defined with minimum and maximum target heart rates. A minimum target heart rate for a patient can be ascertained clinically as a heart rate adequate to sustain the patient at rest, and the programmed lower rate limit or LRL of the pacemaker is set to this rate. A maximum allowable pacing rate or MPR is defined, e.g., using a formula that depends on the patient's age. The rate-response curve then maps a resting exertion level to the minimum heart rate or LRL and maps the maximum exertion level attainable by the patient, termed the maximum exercise capacity, to the maximum allowable heart rate. The responsiveness of the control system, defined as how the sensor-indicated rate changes with a given change in exertion level, depends upon the slope of the rate-response curve (or slopes in the case of a dual-slope curve).

Figure 3:
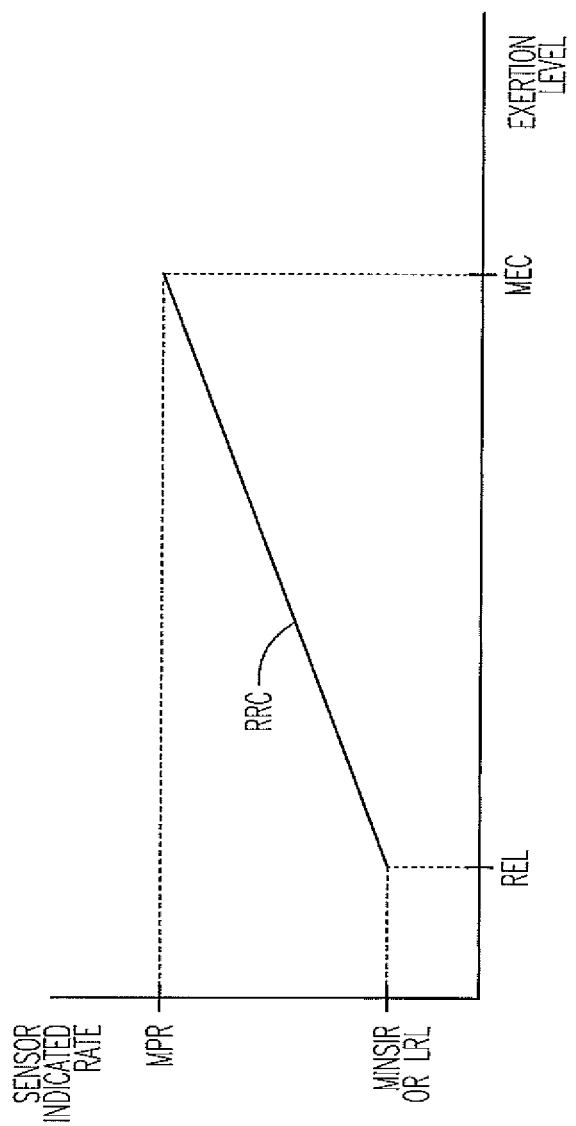
FIG. 3 illustrates a rate-response curve.

An example of a rate-response curve RRC is shown in FIG. 3. Other embodiments may use a dual-slope curve or a non-linear curve. A change in exertion level as determined from a minute ventilation measurement causes a proportional change in the sensor-indicated rate in accordance with the slope of the curve, termed the response factor RF. (It should be appreciated that, as the term is used herein, the measured minute ventilation produced by a transthoracic impedance sensor is actually an ohmic impedance signal related to the true minute ventilation value by appropriate scaling.) The sensor-indicated rate is then used by the pacemaker to pace the heart in accordance with a programmed pacing mode. As shown in the figure, the rate response curve maps a resting exertion level REL to a minimum target rate MinSIR which corresponds to the programmed LRL of the pacemaker. The maximum pacing rate MPR is the maximum rate at which the pacemaker is allowed to pace the heart and is mapped to by the rate response curve from the maximum exertion level the patient is expected to be able to reach, referred to as the maximum exercise capacity MEC. The sensor-indicated rate is then calculated from the measured exertion level EXL as:

$$SIR = LRL + RF \ast EXL$$

In the case where minute ventilation is used as a measure of exertion level, the sensor-indicated rate is computed as:

$$SIR = LRL + RF \ast MV$$

where MV is the measured minute ventilation. The SIR is thus always greater or equal to the LRL, and is limited by the programmed MPR.

Automatic Setting of Response Factor

A device that performs automatic setting of the response factor RF via activity monitoring will now be described. As illustrated above, the pacemaker includes pacing circuitry for generating pacing pulses to be delivered to one or more atrial or ventricular sites, a minute ventilation sensor for measuring minute ventilation, an accelerometer for measuring activity level, and a controller for controlling the delivery of pacing pulses in accordance with a programmed mode and to deliver pacing pulses at a sensor-indicated rate determined by a rate-adaptive algorithm as a function of the sensed minute ventilation. The sensor-indicated rate is computed by mapping a measured ventilation value equaling a specified baseline minute ventilation value (BMV) to a specified minimum pacing rate, termed the lower rate limit (LRL), and mapping a measured minute ventilation value greater than the baseline minute ventilation value to a pacing rate calculated as the LRL added to the amount by which measured minute ventilation value exceeds the baseline minute ventilation value multiplied by a rate response factor. The controller is further programmed to limit the sensor-indicated rate to a specified maximum rate. The controller may be further programmed to calculate the sensor-indicated rate as function of both the measured ventilation value and the measured activity level using separate response factors and/or to calculate the sensor-indicated rate according to a dual-slope rate response curve having separate response factors for lower and higher minute ventilation values.

Figure 4:
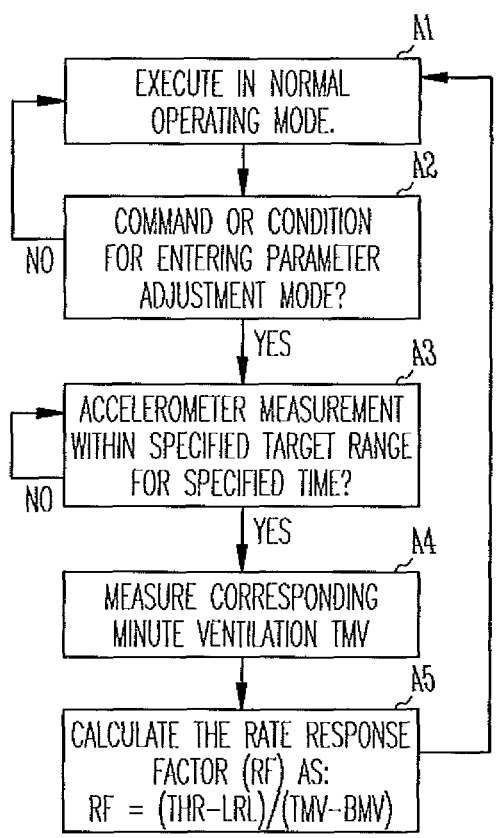
FIG. 4 illustrates an exemplary algorithm for switching between a normal mode and a parameter adjustment mode.

In order to calculate the value of the rate response factor for the minute ventilation sensor, the device enters a parameter adjustment mode. As illustrated in FIG. 4, the device operates in a normal operating mode at step A1 until a command or detected condition monitored for at step A2 causes the device to enter the parameter adjustment mode. In the parameter adjustment mode, the device controller performs the following as illustrated by steps A3 through A5 in FIG. 4: 1) monitor the measured activity level, 2) when the measured activity level is maintained within a specified target activity level range for a specified length of time, measure a corresponding target minute ventilation value (TMV), and 3) calculate the rate response factor (RF) as:

$$RF = (THR - LRL)/(TMV - BMV)$$

where the target heart rate THR is a specified value corresponding to a desired pacing rate for the target activity level range.

The predetermined length of time during which the specified target activity level is to be maintained in order to measure the TMV constitutes a search period. The controller may be further programmed such that, if the patient fails to maintain activity at the specified target activity level for the specified length of time (e.g., 2 minutes), the search period recommences. A variety of other conditions can also be used to cause the search period to recommence such as internal changes to the minute ventilation sensor which cause the minute ventilation data to become invalid (e.g. minute ventilation measurement is suspended due to noise or due to a change of current level used to measure the transthoracic impedance). The search period could continue on for a predetermined number of search periods if necessary.

The controller may be further programmed with a maximum and minimum limit values or the response factor. Also, during the parameter adjustment mode, the device may be operated with a default response factor value to provide adequate rate-adaptive pacing to those patients that require an elevated heart rate in order to reach the target activity level.

The target activity level range may correspond to the activity level of a casual walk, with the target heart rate for that activity level set a rate above the LRL appropriate for the particular patient. The specified length of time for the target activity level to be maintained may be set to any value found to result in a reliable measurement such as two minutes or greater. The target minute ventilation may be measured over some percentage of the specified length of time (e.g., 50% or one minute of a two minute period. It has been found that a one minute period is usually adequate for minute ventilation to reach a steady-state value for a given activity level. The controller may programmed to enter the parameter adjustment mode upon receiving a telemetry command to do so, at periodic intervals, and/or in response to other detected conditions such as any condition which causes a recalibration of the baseline minute ventilation value (BMV). Examples of the latter could include: 1) change of lead vectors which measure thoracic impedance (e.g., the lead impedance of the current vector is measured out of range causing a secondary vector to be used), 2) a warm reset of the device, and 3) a shut off and turn on of the MV sensor due to a tachyarrhythmia episode.

As described above, the target activity level may be set by a physician to any value that the patient may be expected to reach and maintain for a long enough time to properly calibrate the rate-response function of the pacemaker. For example, the device allows the physician to set the activity level to correspond to any walking speed deemed to be casual walking for a given patient. (The device may also be programmed with a function that maps nominal walking speeds to nominal activity levels in order to allow the physician to set the target activity level to a specified value by specifying a particular walking speed rather than a particular activity level.) In the case where the target activity level is to correspond to a casual walk, the physician may set the target activity level to a nominal value (i.e., an activity level that corresponds to a 2 mph walk) or to any selected value that corresponds to an individual patient's speed of casual walking In another embodiment, if the target activity level is not reached by the patient within some specified time period, the implantable device is configured to increase and/or decrease the target activity level according to a predetermined sequence. The device may be configured to continue adjustments of the target activity level until the patient reaches the target activity level for the specified length of time. The device also may be configured to revert to a nominal value if the patient fails to reach and maintain any target activity level within some specified time period.

In one particular example, the device is programmed with a target activity level corresponding to a slow casual walk level (i.e., 2 mph). After a fixed period of time (e.g. 1 hour), if the patient has not remained in the target accelerometer range for the required 2 minutes, the target activity level is changed to the next setting (e.g., an activity level corresponding to a casual walk of 2.5 mph). The device then waits for a fixed period of time (e.g. 1 hour) to see if there is 2 minutes of accelerometer activity within this range. If not, the device resets the casual walk rate back to 2 mph and repeats.

The invention has been described in conjunction with the foregoing specific embodiments. It should be appreciated that those embodiments may also be combined in any manner considered to be advantageous. The same method for setting the response factor could also be used for exertion level sensors other than a minute ventilation sensor. Also, many alternatives, variations, and modifications will be apparent to those of ordinary skill in the art. Other such alternatives, variations, and modifications are intended to fall within the scope of the following appended claims.

What is claimed is:

1. A pacemaker, comprising:

pacing circuitry for generating pacing pulses to be delivered to one or more atrial or ventricular sites;

a minute ventilation sensor for measuring minute ventilation (MV);

an activity level sensor for measuring activity level; and, a controller for controlling the delivery of pacing pulses in accordance with a programmed mode, wherein the controller is further programmed to:

deliver pacing pulses at a rate determined by a rate-adaptive algorithm as a function of the sensed minute ventilation, termed the sensor-indicated rate (SIR);

compute the sensor-indicated rate by mapping a measured ventilation value equaling a specified baseline minute ventilation value (BMV) to a specified minimum pacing rate, termed the lower rate limit (LRL), and mapping a measured minute ventilation value greater than the baseline minute ventilation value to a pacing rate calculated as the LRL added to the amount by which the measured minute ventilation value exceeds the baseline minute ventilation value multiplied by a rate response factor; and, enter a parameter adjustment mode for calculating the value of the rate response factor by: 1) monitoring the measured activity level, 2) when the measured activity level is maintained within a specified target activity level range for a specified length of time, measuring a corresponding target minute ventilation value (TMV), and 3) calculating the rate response factor (RF) as:

$$RF=(THR-LRL)/(TMV-BMV)$$

where the target heart rate THR is a specified value corresponding to a desired pacing rate for the target activity level range and wherein the target activity level range is selected such that the TMV is less than a minute ventilation value that is mapped by the rate-adaptive algorithm to a maximum sensor-indicated rate.

2. The pacemaker of claim 1 wherein the target activity level range corresponds to the activity level of a casual walk.

3. The pacemaker of claim 1 wherein the specified length of time for the target activity level to be maintained is two minutes or greater.

4. The pacemaker of claim 1 wherein the controller is further programmed to calculate the sensor-indicated rate as function of both the measured ventilation value and the measured activity level using separate response factors.

5. The pacemaker of claim 1 wherein the controller is programmed to calculate the sensor-indicated rate according to a dual-slope rate response curve having separate response factors for lower and higher minute ventilation values.

6. The pacemaker of claim 1 wherein the controller is further programmed to increase and/or decrease the target activity level according to a predetermined sequence if the target activity level is not reached within a specified time period.

7. The pacemaker of claim 1 wherein the minute ventilation sensor is a transthoracic impedance sensor and the measured minute ventilation is an ohmic impedance signal related to true minute ventilation value by appropriate scaling.

8. The pacemaker of claim 1 wherein the controller is programmed to enter the parameter adjustment mode upon receiving a telemetry command to do so.

9. The pacemaker of claim 1 wherein the controller is programmed to enter the parameter adjustment mode at periodic intervals.

10. The pacemaker of claim 1 wherein the controller is programmed to enter the parameter adjustment mode in response to a detected condition which causes a recalibration of the baseline minute ventilation value (BMV).

11. The pacemaker of claim 1 wherein the detected condition which causes a recalibration of the baseline minute ventilation value (BMV) is a change of lead vectors used to measure thoracic impedance.

12. The pacemaker of claim 1 wherein the detected condition which causes a recalibration of the baseline minute ventilation value (BMV) is a warm reset of the pacemaker.

13. The pacemaker of claim 1 wherein the detected condition which causes a recalibration of the baseline minute ventilation value (BMV) is a shut off and turn on of the minute ventilation sensor due to a tachyarrhythmia episode.

14. The pacemaker of claim 1 wherein the activity level sensor is an accelerometer.

\* \* \* \* \*